United States Patent [19]

Fossetta et al.

[11] Patent Number: 5,744,340
[45] Date of Patent: Apr. 28, 1998

[54] EXPRESSION OF HUMAN INDUCIBLE NITRIC OXIDE SYNTHASE

[75] Inventors: James D. Fossetta, Roseland; Charles A. Lunn, Somerville; Daniel Lundell, Flemington, all of N.J.

[73] Assignee: Schering Corporation, Kenilworth, N.J.

[21] Appl. No.: 488,702

[22] Filed: Jun. 9, 1995

[51] Int. Cl.$^6$ .............. C12N 9/02; C12N 1/20; C12N 15/00; C12P 21/06
[52] U.S. Cl. .............. 435/189; 435/69.1; 435/252.3; 435/252.33; 435/320.1; 536/23.2
[58] Field of Search .............. 435/69.1, 252.3, 435/320.1, 189, 252.33; 536/23.2

[56] References Cited

U.S. PATENT DOCUMENTS 5,132,407  7/1992  Stuehr et al. .............. 530/395
5,468,630  11/1995  Billiar et al. .............. 435/189

FOREIGN PATENT DOCUMENTS

WO 94/12645  6/1994  WIPO .............. C07K 15/06
WO 94/23038  10/1994  WIPO
WO 94/24269  10/1994  WIPO .............. C07K 15/06

OTHER PUBLICATIONS

Fossetta et al., 1996, *FEBS Lett.*, 379:135–138.
Hearn et al., 1992, *The Journal of Experimental Medicine*, 176:599–604.
Hokari et al., 1994, *J. Biochem.* (Tokyo)116:575–581.
Sherman et al., 1993, *Biochemistry*, 32:11600–11605.
Evans et al., *Proc. Natl. Acad. Sci. USA.*, 89:5361–5365 (1992).
Hevel et al., Journal of Biological Chemistry, 266:22789–22791 (1991).
Iida et al., Journal of Biological Chemistry, 267:25385–25388 (1992).
Knowles et al., *Biochem J.*, 270:883–836 (1990).
Lowenstein et al., *Proc. Natl. Acad. Sci. USA*, 89:6711–6715 (1992).
Lyons et al., Journal of Biological Chemistry, 267:6370–6374 (1992).
Nussler et al., Membrane Biochemistry and Biophysics (5195–5196), Abstr. No. 5200.
Nussler et al., J. Exp. Med. 176:261–264 (1992).
Stuehret et al., *Proc. Natl. Acad. Sci. USA*, 88:7773–7777 (1991).
Tayeh et al., Journal of Biological Chemistry 264:19654–19658 (1989).
Xie et al., Science 256:225–228 (1992).
Yui et al., Journal of Biological Chemistry 266:12544–12547 (1991).
West et al. (1988) Protein Engineering 2(4): 307–311.

*Primary Examiner*—Robert A. Wax
*Assistant Examiner*—Tekchand Saidha
*Attorney, Agent, or Firm*—Cynthia L. Foulke; Immac J. Thampoe

[57] ABSTRACT

Biologically active human inducible nitric oxide synthase (iNOS) is expressed in *E. coli*. The expression of soluble, active iNOS is dependent on its coexpression with calmodulin.

13 Claims, 8 Drawing Sheets

| | | |
|---|---|---|
| A. #4219 | 5' | CGGGAAGCTTGCCGCCAACCATGGCCTGTCCTTGGAAATTCTGTTCAAG 3' |
| B. #4220 | 5' | CAGTTCCCGAAACCACTCGTATTTG 3' |
| C. #4221 | 5' | CGTGACCCTGAGCTCTTCGAAATCC 3' |
| D. #4200 | 5' | TTGGCCATCCTCAGAGGAGAGTCC 3' |
| E. #4199 | 5' | ACAACAAATTCAGGTACGCTGTGTTT 3' |
| F. #4222 | 5' | GTTGCTGCCAGAAAACTGCGGAAGGG 3' |
| G. #4225 | 5' | AGTGCCCTGCTTTGTGCGGAATGCC 3' |
| H. #4226 | 5' | CGCCCTCTAGATCAGAGCGCTGACATCTCCAGGCTGCTGGGCTGC 3' |
| I. #4217 | 5' | AAGCTAGATCTCCATGGCTCGAGATGCATGCTAGCGGATCCGGGCCCCTCTAGAAGTAC 3' |
| J. #4218 | 5' | TTCTAGAGGGCCCGGATCCGCTAGCATGCATCTCGAGCCATGGAGATCTA 3' |
| K. #4230 | 5' | GATCAGCAAGCTTGCT 3' |
| L. #4498 | 5' | GATCCATTCTAGAAGATCTAGTCCATGGACTAGTACCTCCTC 3' |
| M. #4497 | 5' | CTAGGAGGAGGTACTAGTCCATGGCTAGATCTTCTAGAATG 3' |
| N. #4513 | 5' | GACGCCATGGCTGACCAACTGACTGAAGAG 3' |
| O. #4514 | 5' | CCATGGATCCCTCACTTTGCTGTCATTGTAC 3' |

FIGURE 1

SEQUENCE LISTING ( 1 ) GENERAL INFORMATION:

( i i i ) NUMBER OF SEQUENCES: 15

( 2 ) INFORMATION FOR SEQ ID NO: 1:

( i ) SEQUENCE CHARACTERISTICS:
        ( A ) LENGTH: 50 bases ( B ) TYPE: nucleic acid
( C ) STRANDEDNESS: single
( D ) TOPOLOGY: linear ( x i ) SEQUENCE DESCRIPTION: SEQ ID NO: 1:

CGGGAAGCTT GCCGCCAACC ATGGCCTGTC CTTGGAAATT TCTGTTCAAG    50

( 2 ) INFORMATION FOR SEQ ID NO: 2:

( i ) SEQUENCE CHARACTERISTICS:
      ( A ) LENGTH: 25 bases
      ( B ) TYPE: nucleic acid
      ( C ) STRANDEDNESS: single
      ( D ) TOPOLOGY: linear.

( x i ) SEQUENCE DESCRIPTION: SEQ ID NO: 2:

CAGTTCCCGA AACCACTCGT ATTTG    25

( 2 ) INFORMATION FOR SEQ ID NO: 3:

( i ) SEQUENCE CHARACTERISTICS:
      ( A ) LENGTH: 25 bases
      ( B ) TYPE: nucleic acid
      ( C ) STRANDEDNESS: single
      ( D ) TOPOLOGY: linear ( x i ) SEQUENCE DESCRIPTION: SEQ ID NO: 3:

CGTGACCCTG AGCTCTTCGA AATCC    25

( 2 ) INFORMATION FOR SEQ ID NO: 4:

( i ) SEQUENCE CHARACTERISTICS:
      ( A ) LENGTH: 25 bases
      ( B ) TYPE: nucleic acid
      ( C ) STRANDEDNESS: single
      ( D ) TOPOLOGY: linear ( x i ) SEQUENCE DESCRIPTION: SEQ ID NO: 4:

TTGGCCATCC TCAGAGGAGA GTTCC    25

( 2 ) INFORMATION FOR SEQ ID NO: 5:

( i ) SEQUENCE CHARACTERISTICS:
      ( A ) LENGTH: 26 bases
      ( B ) TYPE: nucleic acid
      ( C ) STRANDEDNESS: single
      ( D ) TOPOLOGY: linear ( x i ) SEQUENCE DESCRIPTION: SEQ ID NO: 5:

ACAACAAATT CAGGTACGCT GTGTTT    26

( 2 ) INFORMATION FOR SEQ ID NO: 6:

( i ) SEQUENCE CHARACTERISTICS:
      ( A ) LENGTH: 25 bases
      ( B ) TYPE: nucleic acid
      ( C ) STRANDEDNESS: single
      ( D ) TOPOLOGY: linear ( x i ) SEQUENCE DESCRIPTION: SEQ ID NO: 6:

GTTGCTGCCA GAAACTGCGG AAGGG    25

( 2 ) INFORMATION FOR SEQ ID NO: 7:

( i ) SEQUENCE CHARACTERISTICS:
      ( A ) LENGTH: 25 bases
      ( B ) TYPE: nucleic acid
      ( C ) STRANDEDNESS: single ( D ) TOPOLOGY: linear ( x i ) SEQUENCE DESCRIPTION: SEQ ID NO: 7:

AGTGCCCTGC TTTGTGCGGA ATGCC                                                                25

( 2 ) INFORMATION FOR SEQ ID NO: 8:

( i ) SEQUENCE CHARACTERISTICS:
            ( A ) LENGTH: 44 bases
            ( B ) TYPE: nucleic acid
            ( C ) STRANDEDNESS: single
            ( D ) TOPOLOGY: linear ( x i ) SEQUENCE DESCRIPTION: SEQ ID NO: 8:

CGCCTCTAGA TCAGAGCGCT GACATCTCCA GGCTGCTGGG CTGC                            44

( 2 ) INFORMATION FOR SEQ ID NO: 9:

( i ) SEQUENCE CHARACTERISTICS:
            ( A ) LENGTH: 58 bases
            ( B ) TYPE: nucleic acid
            ( C ) STRANDEDNESS: single
            ( D ) TOPOLOGY: linear ( x i ) SEQUENCE DESCRIPTION: SEQ ID NO: 9:

AAGCTAGATC TCCATGGCTC GAGATGCATG CTAGCGGATC CGGGCCCTCT AGAAGTAC            58

( 2 ) INFORMATION FOR SEQ ID NO: 10:

( i ) SEQUENCE CHARACTERISTICS:
            ( A ) LENGTH: 50 bases
            ( B ) TYPE: nucleic acid
            ( C ) STRANDEDNESS: single
            ( D ) TOPOLOGY: linear ( x i ) SEQUENCE DESCRIPTION: SEQ ID NO: 10:

TTCTAGAGGG CCCGGATCCG CTAGCATGCA TCTCGAGCCA TGGAGATCTA                      50

( 2 ) INFORMATION FOR SEQ ID NO: 11:

( i ) SEQUENCE CHARACTERISTICS:
            ( A ) LENGTH: 16 bases
            ( B ) TYPE: nucleic acid
            ( C ) STRANDEDNESS: single
            ( D ) TOPOLOGY: linear ( x i ) SEQUENCE DESCRIPTION: SEQ ID NO: 11:

GATCAGCAAG CTTGCT                                                                          16

( 2 ) INFORMATION FOR SEQ ID NO: 12:

( i ) SEQUENCE CHARACTERISTICS:
            ( A ) LENGTH: 41 bases
            ( B ) TYPE: nucleic acid
            ( C ) STRANDEDNESS: single
            ( D ) TOPOLOGY: linear ( x i ) SEQUENCE DESCRIPTION: SEQ ID NO: 12:

GATCCATTCT AGAAGATCTA GCCATGGACT AGTACCTCCT C                               41

( 2 ) INFORMATION FOR SEQ ID NO: 13:

( i ) SEQUENCE CHARACTERISTICS:
            ( A ) LENGTH: 41 bases
            ( B ) TYPE: nucleic acid
            ( C ) STRANDEDNESS: single
            ( D ) TOPOLOGY: linear ( x i ) SEQUENCE DESCRIPTION: SEQ ID NO: 13:

CTAGGAGGAG GTACTAGTCC ATGGCTAGAT CTTCTAGAAT G     41

( 2 ) INFORMATION FOR SEQ ID NO: 14:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( x i ) SEQUENCE DESCRIPTION: SEQ ID NO: 14:

GACGCCATGG CTGACCAACT GACTGAAGAG     30

( 2 ) INFORMATION FOR SEQ ID NO: 15:

( i ) SEQUENCE CHARACTERISTICS:
        ( A ) LENGTH: 31 bases
        ( B ) TYPE: nucleic acid
        ( C ) STRANDEDNESS: single
        ( D ) TOPOLOGY: linear ( x i ) SEQUENCE DESCRIPTION: SEQ ID NO: 15:

CCATGGATCC TCACTTTGCT GTCATTTGTA C     31

EXPRESSION OF HUMAN INDUCIBLE NITRIC OXIDE SYNTHASE

FIELD OF THE INVENTION

The invention relates to the expression and purification of human nitric oxide synthase (NOS). In particular, the invention is directed to expression of active human inducible NOS (iNOS) in *Escherichia coli*.

BACKGROUND OF THE INVENTION

Nitric oxide (NO) is an important pleiotropic mediator of many biological responses. NO is derived from the amino acid L-arginine. Nitric oxide synthase (NOS) catalyzes a NADPH-dependent conversion of arginine to citrulline and NO. NOS acts upon arginine to oxidize one of the guanidino nitrogens to NO. The reaction requires five electrons and consumes two moles of oxygen.

Three isoforms of NOS, which roughly define three areas of NO involvement, have been so far described—endothelial cell (eNOS, blood pressure regulation), brain or neuronal (bNOS, neurotransmitter activity), and macrophage or inducible (iNOS, cytostatic and cytotoxic activity against pathogens). The three NOS isozymes share about 50% amino acid sequence homology. All appear to be homodimers with subunit molecular weights of 125–150 kD. Bound cofactors include FAD, FMN, tetrahydrobiopterin (THB), calmodulin and heme (of a cytochrome P450-type spectrally). All appear to make NO by the same overall mechanism. Marietta, 1993, *J. Biol. Chem.* 268:12231–12234. The enzyme mechanism most likely involves passage of electrons from NADPH through FMN/FAD to heme and then to arginine. Calmodulin binding seems to act as a trigger to allow electrons to flow from the flavins to the heme. The role of THB in the mechanism is not yet understood. The carboxy terminal half shows homology to cytochrome P450 reductase with binding sites identified by homology for FMN, FAD, and NADPH. The amino terminal region is not homologous to any other protein and probably contains binding sites for heme, arginine and THB. A calmodulin binding site is found near the middle of all three NOS enzymes.

NOS isozymes are generally classified into two distinct categories or systems—1) a constitutively expressed $Ca^{2+}$/calmodulin-dependent system, and 2) a cytokine-inducible calmodulin-independent system. These two systems exhibit differences in regulation of expression, cofactor dependence, tissue distribution and subcellular localization.

Endothelial NOS and bNOS are constitutive enzymes of limited tissue distribution which are present in low amounts The activity of eNOS and bNOS is regulated by calcium/calmodulin. NO produced by these isoforms serves a signaling purpose. Constitutive production of nanomolar amounts of NO by endothelial cells appears to be vital to the regulation of homeostasis. Additionally, constitutive production of NO is critical for signal transduction in the central nervous system. Activation of guanylyl cyclase by NO is one of the major targets of the constitutive NOS system.

Inducible NOS is only present after cytokine (e.g., bac--terial lipopolysaccharide, interferon-γ, interleukin-1 and tumor necrosis factor) induction. The iNOS system is upregulated by cytokines in almost every cell type examined. In contrast to eNOS and bNOS, activity of iNOS is independent of $Ca^{2+}$ stimulation. Although enzyme activity is not regulated by calcium, iNOS contains tightly bound calmodulin. The level of NO production by iNOS is considerably greater than that of eNOS and bNOS. Due to the higher level of iNOS expressed, this isoform typically synthesizes 100–1000 times as much NO as eNOS and bNOS.

High level NO production is cytotoxic. It is generally known by those skilled in the art that the larger quantities of NO produced by iNOS have antimicrobial (*J. Clin. Invest.*, 1989, 81:1129–1136) and antitumor (*Science*, 1987, 235:473–476) functions. NO is reported to be involved in the killing of parasites, bacteria, tumor cells and viruses. The higher concentration of NO synthesized by iNOS explains the cytotoxic/cytostatic effects of this enzyme. Thus iNOS is an important effector molecule in immunity.

While it is understood by those skilled in the art that NO has both normal physiologic intracellular and extracellular regulatory functions, excessive production of NO is detrimental. High concentrations of NO due to chronic, inappropriate or excess expression of iNOS have been implicated in tissue damage and inflammation especially in certain autoimmune diseases. The iNOS isozyme found in macrophages, monocytes, liver, etc., produces micromolar amounts of NO which contribute to local tissue damage and systemic hypertension which accompanies septic shock and other inflammatory disorders. For example, when vascular smooth muscle cells are stimulated to express NOS in blood vessels by bacterial endotoxin such as lipopolysaccharide (LPS) and inflammatory cytokines that are elevated in sepsis, the excess amounts of nitric oxides that are produced results in massive dilation of blood vessels and sustained hypotension commonly encountered in septic shock. *Proc. Natl. Acad. Sci. USA*, 1990, 87:3629–3632. *FEBS Lett.*, 1990, 265:133–136. It is known that overproduction of nitric oxide in the lungs stimulated by immune complexes directly damages the lungs. *J. Immun.*, 1992, 148:3886. Induction of NOS in pancreatic islets impairs insulin secretion and contributes to the onset of juvenile diabetes. *J. Biol. Chem.*, 1991, 266:21351.

Inhibitors of NOS have been shown to ameliorate disease states in which NO contributes to pathology. Most cases, however, have used nonselective inhibitors of NOS, such as N-methylarginine (NMMA). Nonselective inhibitors have hypertensive effects through inhibition of eNOS. While these side effects may be tolerably for acute use such as in septic shock, it would be desirable to have inhibitors that are selective to iNOS for chronic cases.

Human eNOS, bNOS and iNOS have been cloned. Endothelial NOS has been cloned from HUVESs. Janssens et al., 1992, J. Biol. Chem. 267:4519. Brain NOS has been cloned from cerebellum. Nakane et al., 1993, *FEBS Letters*, 316:175. Inducible iNOS has been cloned from hepatocytes (Geller et al., 1993, *Proc. Natl. Acad. Sci. U.S.A.*, 90:3491), from chondrocytes (Charles et al., 1993, *Proc. Natl. Acad. Sci. U.S.A.*, 90:11419) and from cholorectal adenocarcinoma (Sherman et al., 1993, 32:1600). All three iNOS clones are identical. The genomic structure containing 26 exons (37 Kb) and 5' flanking region of human iNOS has been described by Chartrain et al., 1994, *J. Biol. Chem.*, 269:6765.

Stable, heterologous expression in eucaryotic cells of the constitutive isoforms of NOS has been described by a number of sources. Since eNOS and bNOS are not active unless calcium levels are raised intracellularly, stable expression without the toxic effects of NO production would be expected. This was first demonstrated with rat bNOS which has been stably expressed in human kidney 293 cells to 2% of total protein. McMillan et al., 1992, *Proc. Natl. Acad. Sci. USA* 89:11141–11145. Rat bNOS has also been expressed in *Spodoptera frugiperda* (Sf9) insect cells after infection with baculovirus containing the bNOS cDNA up to 10% of total protein. Richards and Marietta, 1994, Biochemistry 33:14723–14732. Nakane et al., 1995, *Biochem. Biophys. Res. Comm.* 206:511–517. Expression of active eNOS at low levels has also been described in Sf9 cells after baculovirus infection. Richards and Marletta, 1994, *Biochemistry* 33: 14723–14732. Chen et al., 1994, *J. Biol. Chem.* 269:25062–25066. Lower expression of eNOS may be due to protein aggregation caused by myristoylation as noted by Nakane et al. (*Bioochem. Biophys. Res. Comm.*, 1995, 206:511–517). No equally rich source of human iNOS has been described in the prior art.

In contrast to eNOS and bNOS, iNOS produces NO in an unregulated manner. The toxic effects of NO would be expected to make its stable, unregulated expression in cells very difficult. A stably transfected mammalian cell line expressing human iNOS has only been described in a baculovirus system. While expression in a baculovirus infected Sf9 cells can be a very good expression system, it is not a "stable" system in that it depends on continual reinfection with baculovirus containing iNOS expression cassettes. There thus is need for a stable system for the expression of human iNOS. Bacterial expression, with easy growth and scale-up capacities, would be particularly desirable.

SUMMARY OF THE INVENTION

The present invention provides for the stable expression of human NOS. In particular, the invention provides methods for the high level bacterial production of human NOS. The bacterial production of active NOS is accomplished by coexpressing NOS with calmodulin in a bacterial host.

More particularly, the present invention provides DNA constructs and recombinant vectors which may be used to prepare human NOS. The vectors of the invention comprise DNA constructs encoding human NOS and/or human calmodulin and are capable of directing expression of such DNA in a bacterial expression system. The invention further provides bacterial host cells transformed with such vectors. In a preferred embodiment of the invention, human iNOS is expressed in *E. coli*.

The invention also provides a method of making biologically active human NOS, in particular human iNOS, comprising culturing a transformed bacterium capable of coexpressing human NOS and human calmodulin, and preparing biologically active human NOS from the culture medium.

The invention provides a simple procedure for obtaining a source of human iNOS at yields adequate for spectral and structural analysis. The iNOS obtained may be used to screen for specific inhibitors of iNOS which are capable of specifically inhibiting iNOS without interfering with the essential functions of NOS elsewhere in the body.

BRIEF DESCRIPTION OF THE DRAWING FIGURES

The invention can be more readily understood by referring to the description below, and to the accompanying drawing figures in which:

FIG. 1 shows the nucleotide sequences of the oligonucleotides used as primers for iNOS cloning and expression.

DETAILED DESCRIPTION OF THE INVENTION

Figure 2:
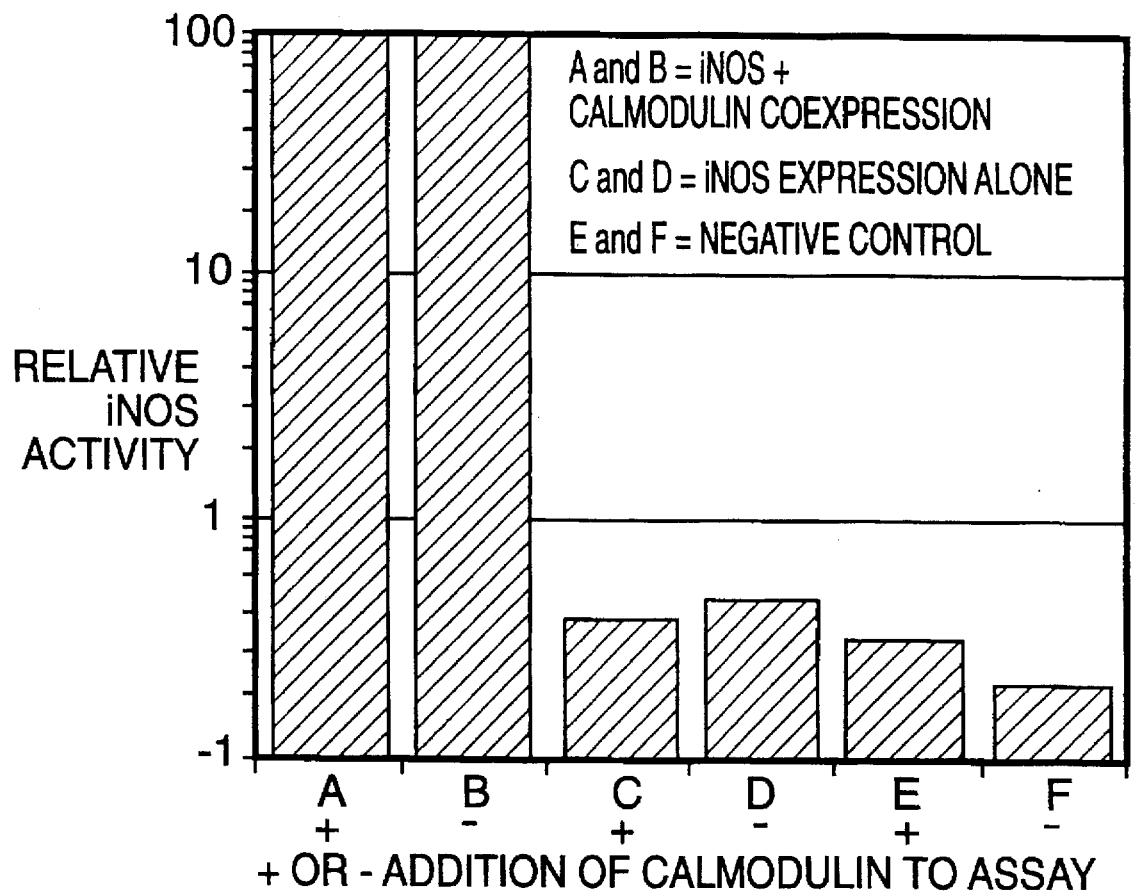
FIG. 2 shows iNOS expression in *E. coli* with and without coexpression of calmodulin.

All references cited herein are hereby incorporated in their entireties, by reference.

It has now been discovered that human iNOS can be stably expressed in *E. coli*. The invention is based on the discovery that the generation of active iNOS surprisingly requires coexpression with calmodulin. Simple expression of iNOS cDNA alone will not result in significant active protein.

DNA constructs of the invention encoding human iNOS may be of genomic or cDNA origin; for instance, they can be obtained by preparing a genomic or cDNA library and screening for DNA sequences coding for all or pair of the iNOS/hybridization using synthetic oligonucleotide probes and standard techniques. Sambrook et al., Molecular Cloning: A Laboratory Manual, 2nd Edition, Cold Spring Harbor, 1989. The DNA construct of the invention encoding the iNOS may also be prepared synthetically by established standard methods, e.g., in an automatic DNA synthesizer, and then purified, annealed, ligated and cloned in suitable vectors. In addition, the DNA constructs may be of mixed synthetic and genomic, mixed synthetic and cDNA or mixed genomic and cDNA origin prepared by ligating fragments of synthetic, genomic or cDNA, the fragments corresponding to various parts of the entire DNA construct, in accordance with standard techniques. The DNA constructs may also be prepared by polymerase chain reaction using specific primers. All of these techniques are well within the skill of the art.

The DNA constructs may contain the entire native sequence of human iNOS or a homologue thereof. The term "homologue" is intended to indicate a natural variant of the DNA sequence encoding human iNOS or a variant produced by modification of the DNA sequence. Examples of suitable modifications of the DNA sequence are nucleotide substitutions which do not give rise to another amino acid sequence of the iNOS or nucleotide substitutions which do give rise to a different amino acid sequence and therefore, possibly, a different protein structure. Other examples of possible modifications are insertions of one or several nucleotides into the sequence, addition of one or several nucleotides at either end of the sequence, or deletion of one or several nucleotides at either end or within the sequence. Any homologous DNA sequence encoding a protein which exhibits iNOS activity (e.g., with respect to substrate specificity) similar to that of the naive protein is contemplated for use in the claimed invention.

DNA constructs encoding human calmodulin or a homologue thereof can likewise be obtained as indicated above.

It will be appreciated by those skilled in the art that the cloned human iNOS and calmodulin cDNAs may be recombinantly expressed by molecular cloning into an expression vector containing a suitable promoter and other appropriate transcription regulatory elements, and transferred into a host cell to produce recombinant iNOS and calmodulin. The procedures used to ligate the DNA sequences of interest, the promoter and the terminator, respectively, and to insert them into suitable vectors containing the information necessary for replication are well known to persons skilled in this art. Expression vectors are defined herein as DNA sequences required for the transcription of cloned copies of genes and the translation of their mRNAs in an appropriate host. Various expression vectors which would be recognized by the skilled artisan as suitable for use in the present invention are commercially available.

The host cell into which the expression vectors of the invention are introduced is preferably a bacterial cell line, more preferably *E. coli*. Various strains of *E. coli* are commercially available and are well known in the art. While expression in *E. coli* is described in detail below, one skilled in the art would recognize that other bacterial host cells may be used for expression.

The iNOS is produced by a method which comprises culturing a host cell as described above in a suitable nutrient medium under conditions which are conductive to the expression of the iNOS and recovering the resulting iNOS from the culture. The medium used to culture the cells may be any conventional medium suitable for growing the bacterial cell line. Suitable media are available from commercial suppliers or may be prepared according to published recipes.

The iNOS produced by the cells may then be recovered from the culture medium by conventional procedures including separating the host cells from the medium by centrifugation or filtration and precipitating the proteinaceous components of the supernatant or filtrate by means of a salt, e.g., ammonium sulfate. Human iNOS is expressed in *E. coli* as an inactive form which can be activated after cell breakage. Biologically active iNOS may be obtained in the crude extracts following addition of THB. The active enzyme can then be further purified using a variety of chromatographic procedures, e.g., ion exchange chromatography, affinity chromatography, or the like. A preferred purification scheme involves ammonium sulfate precipitation followed by Q Sepharose ion exchange and Sephacryl S300 gel filtration fractionation.

EXAMPLE

The following example describes various aspects of the invention in more detail.

CLONING AND EXPRESSION OF iNOS
Cloning of Human iNOS

Human iNOS was cloned from DLD cells (colorectal adenocarcinoma) using protocol similar to that described by Sherman et al., 1993, *Biochemistry* 32:11600–11605). A reverse transcriptase reaction was carried out on 3.2 mg of total RNA from cytokine induced DLD cells in 20 ml using a cDNA Cycle kit (Invitrogen) and an oligo dT primer following the manufacturer's protocol. Two one hour reverse transcriptase reactions were carried out back-to-back to ensure maximal product.

Following the reverse transcriptase reaction, the cDNA was divided into four PCR reactions performed using primers A–H shown in FIG. 1 as follows: reaction 1—primers A+B (using AmpliTaq); reaction 2—primers C+D (using Ultma polymerase); reaction 3—primers E+F (using AmpliTaq); and reaction 4—primers G+H (using AmpliTaq). The nucleotide sequences of primers A–H correspond, respectively, to Sequence ID NOS:1–8. AmpliTaq and Ultma polymerases were purchased from Perkin-Elmer. PCR primers were made on an Applied Biosystem 394C DNA synthesizer. Reaction 1 was run with the following program: 30 sec, 94° C.; 2 min, 55° C.; 2 min 72° C.; 30 cycles. Reactions 2–4 were run with the following program: 1 min, 94° C.; 2 min, 55° C.; 3 min, 72° C; 30 cycles.

Following PCR, the products were phenol/chloroform extracted, ethanol precipitated, and digested for cloning as follows: reaction 1 was cut with HindIII/NcoI; reaction 2 was cut with NcoI/NsiI; reaction 3 was cut with NsiI/BamHI; and reaction 4 was cut with BamHI/XbaI. Restriction enzymes were purchased from New England Biolabs. Digested fragments were isolated after agarose gel electrophoresis using GeneClean (Bio 101) following the manufacturer's protocol and were ligated to appropriately digested pSL1190 (Pharmacia). The ligation mix was electroporated into *E. coli* DH10B (GibcoBRL). Clones were sequenced using an Applied Biosystems 373A DNA Sequencer.

A full length iNOS cDNA was assembled from the products of the four PCR reactions. A vector was made for assembling these fragments sequentially by digesting pUC19 with HindIII/KpnI and ligating the isolated vector with annealed oligonucleotides I and J. The nucleotide sequence of oligonucleotides I and J correspond, respectively, to Sequence ID NO:9 and Sequence ID NO:10. This construct lacked the intended HindIII site due to an error in oligonucleotide I. This was corrected by making oligonucleotide K which is self-annealing and which was ligated into the BglII site created by oligonucleotides I+J to add the needed HindIII site. The nucleotide sequence of oligonucleotide K corresponds to Sequence ID NO: 11. This vector now had correctly placed HindIII, NcoI, NsiI, BamHI, and XbaI sites. The final assembled iNOS cDNA vector was named piNOS17-10.

iNOS Expression Vector

The iNOS cDNA was cloned into pJF123, which contains a tac promoter-lac operator, a laci$^q$ gene, and a pUC19 ampicillin gene and origin. To accept the iNOS cDNA, pJF123 was modified by digesting with XbaI/BamHI, isolating the large fragment, and ligating it with annealed oligonucleotides L and M to make pJF402. The nucleotide sequence of oligonucleotides L and M correspond, respectively, to Sequence ID NOS:12 and 13. This added an NcoI site containing the initiator ATG codon, removed the original XbaI site, and added a new XbaI site downstream of the NcoI site. Vector piNOS17-10 was cut NcoI/XbaI and the iNOS cDNA fragment was isolated. This fragment was ligated with pJF402 cut NcoI/XbaI to make piNOS48-16.

COEXPRESSION OF iNOS WITH CALMODULIN

Calmodulin has been shown to be very tightly associated with murine iNOS (Cho et al., 1992, *J. Exp. Med.* 176:599–604); it is not removed by EGTA or purification. Therefore, calmodulin might be considered to be a subunit of iNOS and thus could be essential for its folding. To test whether coexpression of human iNOS and calmodulin might be required for proper iNOS folding, human calmodulin was cloned from a human brain cDNA library by PCR. An expression vector in pACYC184, which is compatible for cotransfection with the pUC origin of piNOS48-16, was assembled and expression of calmodulin was demonstrated.
Cloning of Human Calmodulin The human calmodulin cDNA was isolated by RT-PCR. One microgram of brain polyA$^+$RNA (Clontech) was reverse transcribed with an oligo dT primer using a cDNA Cycle kit (Invitrogen) following the manufacturer's protocol. Ten percent of the RT reaction was then subjected to PCR with oligonucleotides N and O using AmpliTaq and 25 cycles of the following program: 30 sec, 94° C.; 2 min, 55° C.; 2 min, 72° C. The nucleotide sequences of oligonucleotides N and O correspond, respectively, to Sequence ID NOS: 14 and 15. The PCR product was cut with NcoI/BamHI and the product ligated into pSL1190 cut the same. A correct clone was identified by sequencing. This clone was named pSL1190cam-12.

Calmodulin Expression Vector

To make a calmodulin expression vector, pSL1190cam-12 was digested with NcoI/BamHI and the calmodulin cDNA was isolated. It was ligated to pJF402 cut similarly to make pCam5-2. This vector was then cut with XmnI/AvaI, and the tac-promoted calmodulin+lacI$^q$ fragment was isolated and ligated into pACYC184 (Chang and Cohen, 1978, *J. Bactiol.* 134:1141–1156) cut EcoRV/AvaI to make pACYC:Cam2-1. Vector pACYC:Cam2-1 was transformed into *E. coli* JS5 (BioRad). Following induction with IPTG, expression of calmodulin was demonstrated by a Western blot using an anti-calmodulin monoclonal antibody (Upstate Biotechnology) and by Coomassie staining after SDS-PAGE.

iNOS Assay iNOS activity was measured by the conversion of radioactive arginine to citrulline similar to that described by Bredt and Snyder (*Proc. Natl. Acad. Sci.* USA, 1989, 86:9030–9033). Reactions contained 20 mM HEPES pH 7.5, 1 mM DTT, 10 µM FAD, 10 µM FMN, 20 µM THB, 2 µM hemin, 1 mM NADPH, 2 mg/ml BSA, 50 µM cold arginine and 1 µM $^3$H-arginine (60 Ci/mmole; Amersham). Reactions were carried out at 37° C. for 30–60 minutes and were stopped by addition of one volume of 0.1 M sodium citrate, pH 5.5, 100 mM N$^G$-methyl-L-arginine (NMMA). The reaction mix was then passed through 100 µl of Dowex resin (AG50-X8) in a filtration plate to separate citrulline (unbound) from arginine (bound). The filtrate was counted with one volume of scintillation fluid in 1450 Microbeta Plus liquid scintillation counter (Wallac). Enough enzyme is used per assay point to convert 10–20% of the tritiated arginine to product. Activities of various cell extracts examined are reported in units/ml, units defined as pmoles of citrulline formed per minute. Samples of *E coli* cell lysate expressing iNOS activity were desalted on a G-25 column prior to assay to remove any cold arginine.

Expression of human iNOS in *E. coli* resulted in NOS activity barely detectable above background. Inclusion of calmodulin in the NOS assay had no effect. SDS polyacrylamide gel electrophoresis and Western blotting showed that the expression of soluble iNOS protein was very low.

Purification of iNOS in *E. coli*

*E. coli* JS5 containing piNOS48-16+pACYC:Cam2-1 was grown at 30° C. in 4 liters of Luria broth to an O.D.$_{660}$ of about 1.0. IPTG was then added to 100 µM and the culture was grown overnight. All steps were performed at 4° C. Cells were harvested, resuspended in 20 mM HEPES pH 7.5, 1 mM DTT, 1 mM PMSF, 1 mM EDTA, 2 µM tetrahydrobiopterin (THB; Biomol Research Labs), 2 µM hemin (Sigma), and 10 µM each of FAD and FMN (Buffer A) to O.D.$_{660}$=100, broken by sonication, and centrifuged at 30,000×g for 30 minutes. The supernatant was made 20% saturated ammonium sulfate and centrifuged at 30,000×g for 20 minutes. This supernatant was adjusted to 40% saturated ammonium sulfate and was centrifuged again as above. The pellet was resuspended in buffer B (buffer B=buffer A minus EDTA and flavins) to 1 mg/ml and conductivity <6 mS; CHAPS (Sigma) was added to 0.5% (w/v). The sample was loaded onto a 60 ml Q Sepharose column (Pharmacia) equilibrated in buffer B+50 mM NaCl. After charging the column was washed with one column volume of equilibration buffer followed by a 10 column volume gradient in buffer B from 50 to 300 mM NaCl. The iNOS activity peak was pooled, precipitated with 50% saturated ammonium sulfate, and centrifuged to collect the protein. The pellet was redissolved in 10 ml of buffer B+100 mM NaCl and was loaded onto a 300 ml Sephacryl 300 column equilibrated in the same. iNOS containing fractions >90% pure were pooled.

Figure 3:
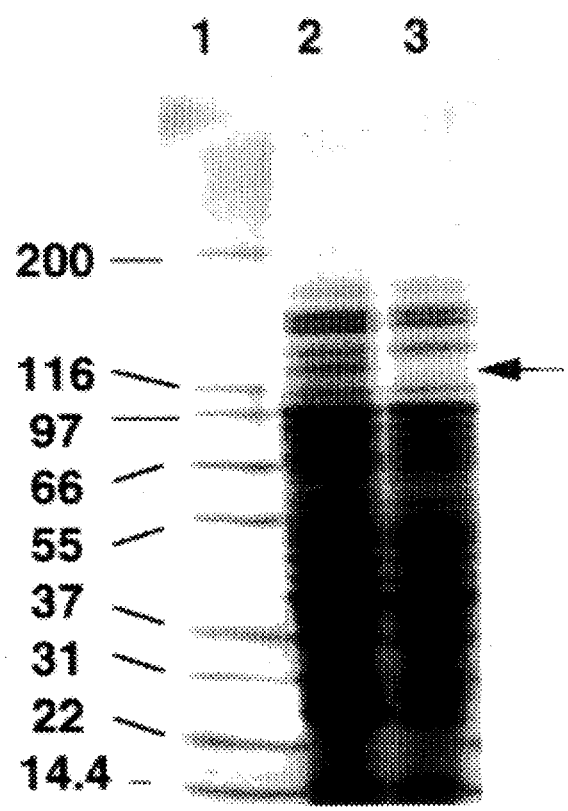
FIG. 3 shows a SDS PAGE of iNOS expression in *E. coli*.

FIG. 2 shows the results of NOS activity when iNOS and calmodulin are coexpressed compared to iNOS expression alone. NOS assays were performed as described above, except 1 µM undiluted labeled arginine was used. When calmodulin was used it was added at 10 µg/ml. Results are normalized to the coexpression extracts (A and B) and are the average of three assays. In column B addition of calmodulin had no effect compared to column A. The level of activity with coexpression is >100 fold that without coexpression. The activity with coexpression is about 3000–5000 units/mg in the crude extract. Assuming a specific activity of 1×10$^6$ units/mg based on murine iNOS (Stuehr et al.,1991, *Proc. Natl. Acad. Sci. USA*, 88:7773–7777), the expression level is about 0.3–0.5% of total soluble protein. This is borne out by SDS PAGE as shown in FIG. 3, where a band corresponding to iNOS is clearly visible at about 125 kD but not in a negative control strain. In FIG. 3, lane 1 is a molecular weight marker set, sizes in kD being shown on the left margin. Lane 2 is piNOS48-16+pACYC:cam 2-1 coexpressed in *E. coli* JS-5. Lane 3 is a negative control. The arrow indicates human iNOS protein.

CHARACTERIZATION OF *E. COLI* EXPRESSED iNOS

The specific activity of iNOS in the crude cell supernatant was estimated from the amount of iNOS on an SDS polyacrylamide gel (by comparison to a BSA control sample) to be 500–1000 nmoles citrulline/min/mg of iNOS. This compares favorably with 1000 nmole/min/mg determined for purified murine iNOS (Stuehr et al., 1991, *Proc. Natl. Acad. Sci. USA*, 88:7773–7777). This indicates that no eucaryotic specific processing is necessary for expression of full iNOS activity.

The iNOS activity in the crude cell extract was further characterized by a number of criteria. The Km for arginine was 8 µM which compares favorably with that determined for human and murine iNOS by others. MacNaul et al., 1994, "1st International Conference on Biochemistry and Molecular Biology of NO", UCLA; abstract # A19. The activity was unaffected by addition of 1 mM EGTA, 1 mM CaCl$_2$, or calcium +10 mg/ml calmodulin.

Figure 4:
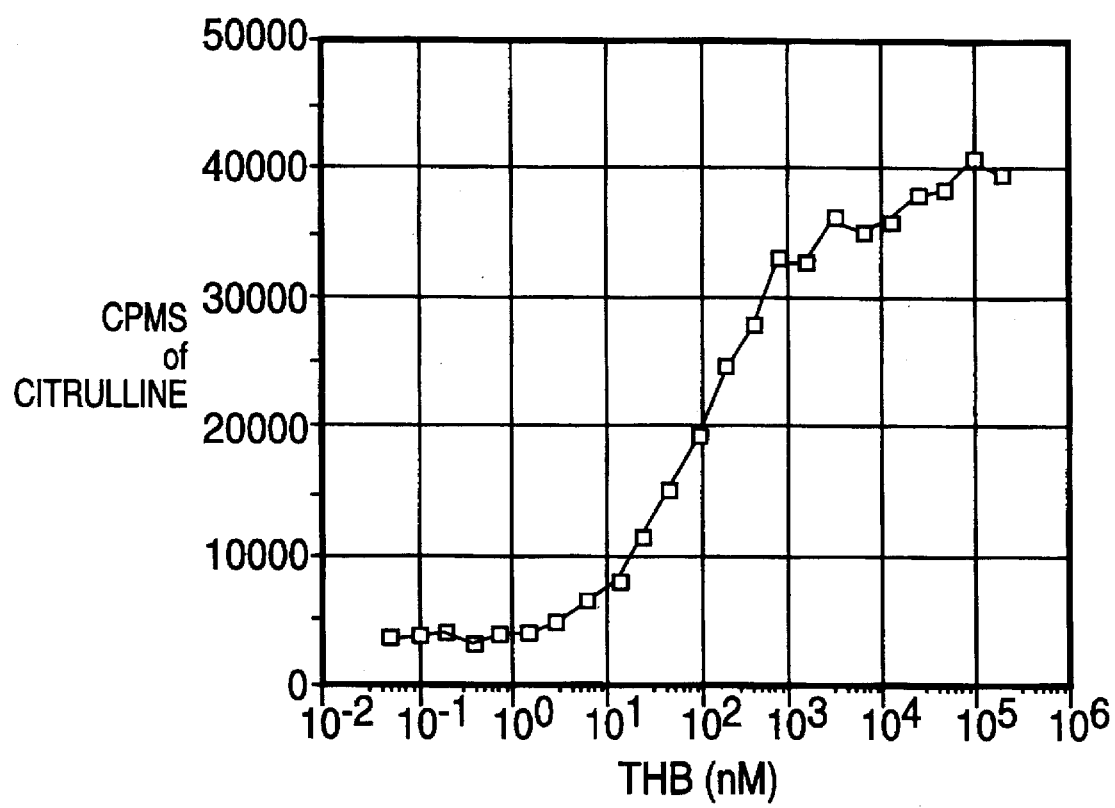
FIG. 4 shows the effect of THB on iNOS activity.

*E. coli* lacks the ability to make THB, which is an essential cofactor of iNOS. When cells are broken in the absence of THB and no THB is added to the NOS assay, no activity is seen. Addition of THB restores NOS activity. A titration curve of THB versus NOS activity is shown in FIG. 4. Cells were broken and processed for activity, as described, except that THB was not added. The assay was then run with varying amounts of THB. Half-maximal activity is seen around 120 nM of THB. This compares favorably with the K$_d$ determined for THB binding to rat bNOS of about 40 nM (Klatt et al., 1994, *J. Bio. Chem.* 269:13861–13866). There was no dependence of activity with the other iNOS cofactors, hemin, FAD, or FMN.

Figure 5:
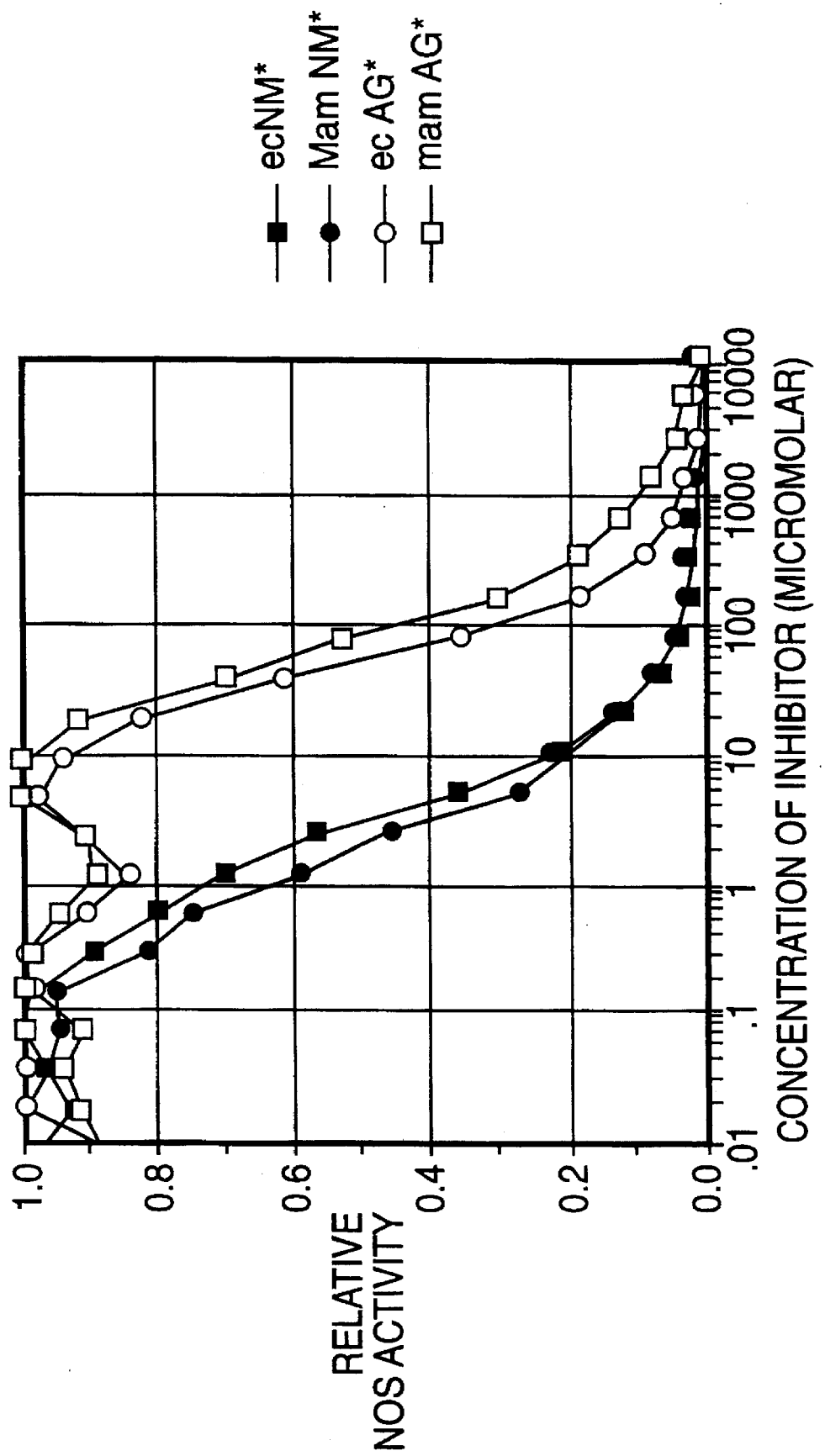
FIG. 5 shows a comparison of the inhibition of *E. coli*-derived iNOS and mammalian cell-derived iNOS using two inhibitors of iNOS.

FIG. 5 shows a comparison of the inhibition of the *E. coli*-derived iNOS with recombinant iNOS prepared in human 293 embryonic kidney cells by NMMA and by aminoguanidine. NMMA and aminoguanidine are two inhibitors of iNOS. Assays were run using a 1 µM labeled arginine and varying concentrations of NMMA and aminoguanidine from 0.01 to 10,000 µM. The two inhibitors have $IC_{50}$'s within two-fold of each other on both sources of iNOS. Similar results were obtained using imidazole as an inhibitor ($IC_{50}$=120 µM).

PURIFICATION OF iNOS

Human iNOS was purified to >90% purity by a three step procedure. The purification consisted of an ammonium sulfate precipitation followed by a Q Sepharose ion exchange and Sephacryl S300 gel filtration fractionation.

Breakage of cells and the ammonium sulfate fractionations were done in the presence of 10 µM FAD, 10 µM FMN, 2 µM THB, and 2 µM hemin. Leaving these cofactors out of the breaking buffer had no effect on the level of iNOS activity. However, when stored overnight at 40° C. in the absence of cofactors half of the activity was lost while in the presence of the cofactors complete activity was retained. Flavins were omitted after the 40% ammonium sulfate fractionation since they bind tightly to Q Sepharose. CHAPS detergent was included for the Q Sepharose column because iNOS fractionated poorly from the bulk of the protein in its absence. The yield of iNOS from about 20 liters of cells (32 g starting protein in the crude extract) was about 30–40 mg.

Figure 6A:
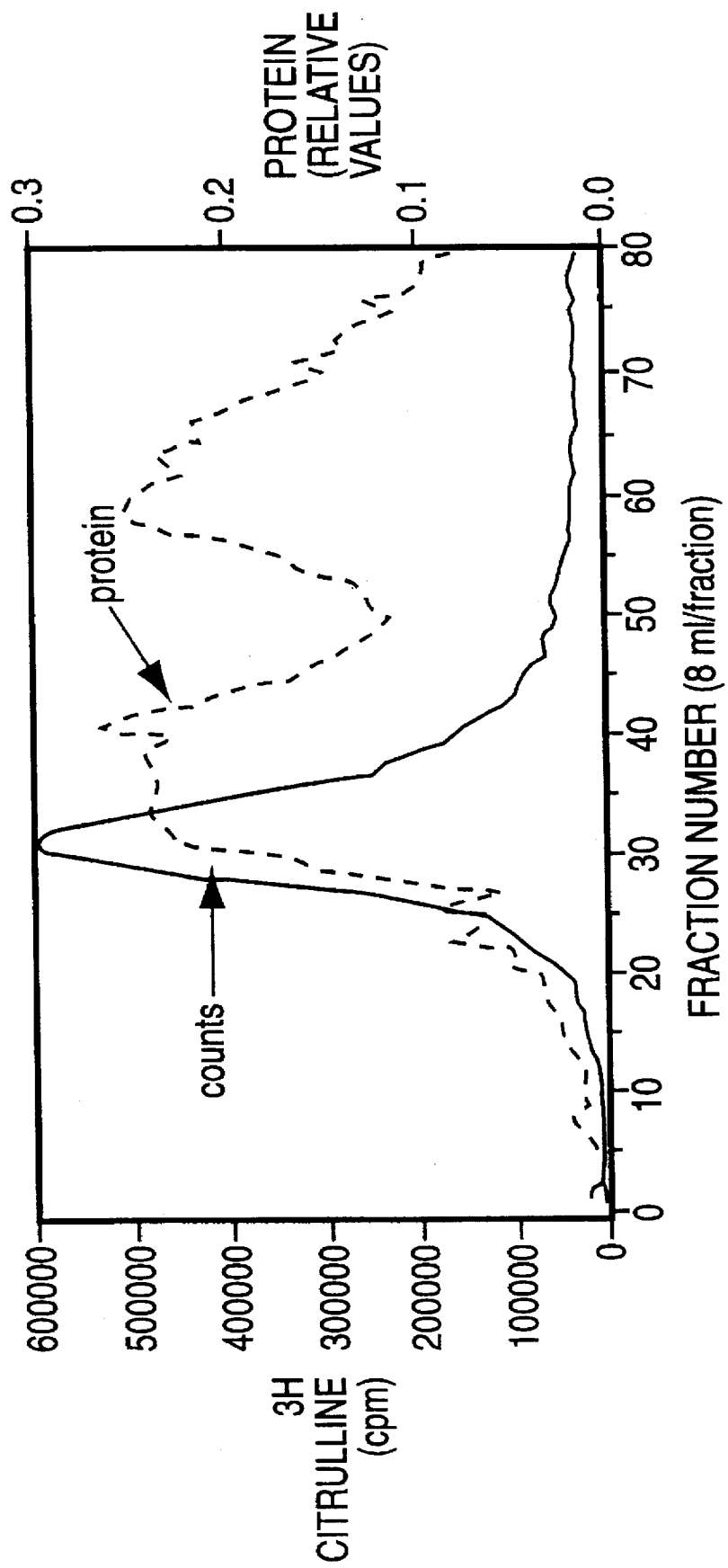
FIG. 6A shows the elution profile of human iNOS from Q Sepharose.
Figure 6B:
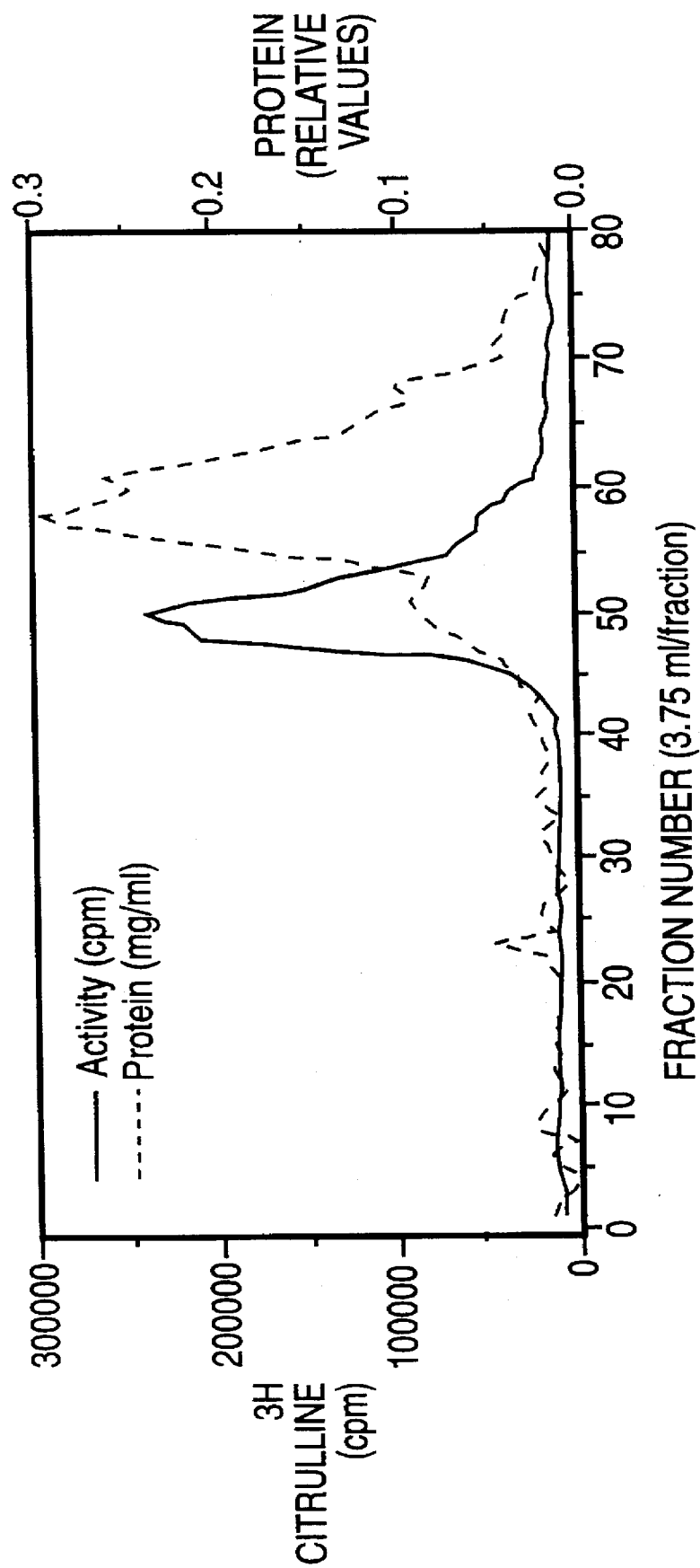
FIG. 6B shows the elution profile of human iNOS from Sephacryl S300.
Figure 7:
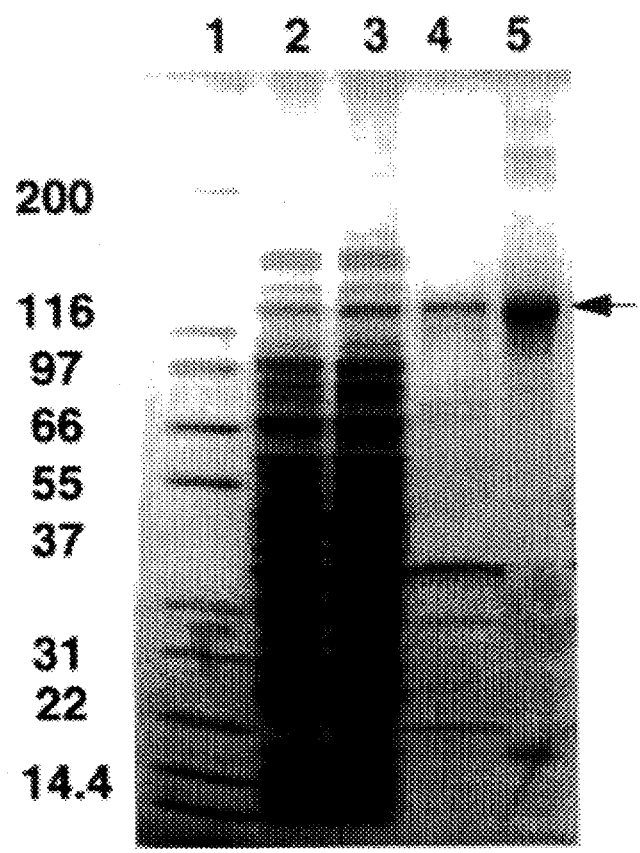
FIG. 7 shows SDS PAGE of the steps during purification of human iNOS from *E. coli*.

The profile from the Q Sepharose and S300 columns are shown in FIGS. 6A and 6B, respectively. FIG. 7 shows an SDS polyacrylamide gel of the steps during the purification. Lane 1, molecular weight markers, sizes in kD being shown on the left margin of this lane. Lane 2, E. coli lysate. Lane 3, 40% ammonium sulfate precipitate. Lane 4, pool from the Q Sepharose. Lane 5, pool from the front half of the S300 iNOS peak (fractions 45–50). The calmodulin band can be seen in lane 5 at about 17 kd. In lane 5 a band corresponding to calmodulin (by Western blot) which copurifies with the human iNOS protein can be seen at about 17 Kd. Overall yield of activity was about 17%. The specific activity of the most pure material (the leading edge of the S300 column which was >95% pure) was 450,000 units/mg. This compares favorably with pure murine iNOS at 1,000,000 units/mg and rat bNOS at 270,000 units/mg.

The results of the purification are summarized in the following Table.

Purification of human iNOS

| Sample | Volume (ml) | Protein Conc. (mg/ml) | Total protein (mg) | Total activity (units) | Specific Activity (units/mg) |
|---|---|---|---|---|---|
| cell lysate | 2600 | 12.5 | 32475 | 78,600,000 | 2,420 |
| 40% ammonium sulfate ppt | 3300 | 1.2 | 3960 | 77,600,000 | 19,600 |
| Q Sepharose pool | 470 | 0.35 | 165 | 23,000,000 | 149,000 |
| S300 pool | 180 | 0.22 | 40 | 13,000,000 | 317,000 |

Human iNOS has now been successfully produced in a bacterial expression system. Expression of soluble, active iNOS has been discovered to be dependent on its coexpression with calmodulin. In the absence of calmodulin, expression of soluble iNOS protein and iNOS activity was barely detectable above the E. coli negative control. While not being bound by any particular theory, it is postulated that the extremely tight association of calmodulin with iNOS serves a structural purpose in allowing iNOS to fold correctly. This is in contrast to eNOS and bNOS where calmodulin binding is regulated by calcium; calmodulin is freely dissociable if calcium is removed by EGTA.

E. coli expressed iNOS exhibits approximately the same specific activity as murine iNOS. It also has the same Km for arginine and $IC_{50}$'s for three inhibitors as does mammalian derived iNOS. This indicates that no mammalian specific modification of iNOS is necessary for NOS activity. The enzyme activity was completely dependent on added THB with a half maximal concentration of 120 nM. The binding constant of THB for bNOS has been shown to be 37 µM and 250 µM, in the presence and absence of 100 µM arginine, respectively (Klatt et al.,1994, J. Biol. Chem. 269:13861–13866).

Expression of iNOS in E. coli overcomes the prior art problems associated with transient expression systems. Stable expression may be due to the lack of THB in E. coli which prevents iNOS activity. The expression of human iNOS in E. coli allows pure iNOS to be obtained by a simple procedure and at yields compatible with spectral and structural analysis. Moreover, the complete dependence of E. coli expressed iNOS on THB offers a unique chance to understand the mechanism of this cofactor in the catalytic mechanism.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

We claim:

1. A transformed bacterial host cell which expresses human inducible nitric oxide synthase (iNOS) iNOS and human calmodulin under conditions permitting the coexpression thereof.

2. The host cell of claim 1 wherein said host cell is *E. coli*.

3. The host cell of claim 1 wherein said host cell is transformed with a DNA construct encoding human inducible nitric oxide synthase and a DNA construct encoding human calmodulin.

4. The host cell of claim 3 wherein said host cell is transformed with a first recombinant vector comprising a DNA construct encoding human inducible nitric oxide synthase and a second recombinant vector comprising a DNA construct encoding human calmodulin.

5. The host cell of claim 3 wherein said host cell is transformed with a recombinant vector comprising a DNA construct encoding human inducible nitric oxide synthase and a DNA construct encoding human calmodulin.

6. A recombinant vector comprising a DNA construct encoding human inducible nitric oxide synthase and a DNA construct encoding human calmodulin, which vector directs expression of human inducible nitric oxide synthase and human calmodulin in a bacterial expression system under conditions permitting the coexpression thereof.

7. A method for producing human iNOS protein comprising:

maintaining recombinant transformed bacterial host cells human inducible nitric oxide synthase and human calmodulin under conditions permitting the coexpression thereof, and obtaining active iNOS from said recombinant transformed host cells.

8. The method of claim 7 wherein said host cell is *E. coli*.

9. The method of claim 7 wherein said host cell is transformed with a first recombinant vector comprising a DNA construct encoding human inducible nitric oxide synthase and a second recombinant vector comprising a DNA construct encoding human calmodulin.

10. The method of claim 7 wherein said host cell is transformed with a recombinant vector comprising a DNA construct encoding human inducible nitric oxide synthase and a DNA construct encoding human calmodulin.

11. The method of claim 7 wherein iNOS is extracted from said host cells.

12. The method of claim 7 wherein said host cells are treated with tetrahydrobiopterin during extraction to obtain active human inducible nitric oxide synthase.

13. The vector of claim 6 wherein said bacterial host cell is *E. coli*.

\* \* \* \* \*